US006261813B1

United States Patent
Khmelnitsky et al.

(10) Patent No.: US 6,261,813 B1
(45) Date of Patent: Jul. 17, 2001

(54) TWO STEP ENZYMATIC ACYLATION

(75) Inventors: Yuri L. Khmelnitsky; Cheryl L. Budde; John M. Arnold, all of Coralville; Joseph O. Rich, Iowa City, all of IA (US); Sharon S. Chen, Pasadena, CA (US); Alexander Ya. Usyatinsky, Coralville, IA (US); Douglas S. Clark, Orinda, CA (US); Jonathan S. Dordick, Schenectady, NY (US)

(73) Assignee: Albany Molecular Research, Inc., Albany, NY (US)

( * ) Notice: Subject to any disclaimer, the term of this patent is extended or adjusted under 35 U.S.C. 154(b) by 0 days.

(21) Appl. No.: 09/198,096

(22) Filed: Nov. 23, 1998

Related U.S. Application Data

(63) Continuation-in-part of application No. 09/091,833, filed as application No. PCT/US96/14573 on Sep. 11, 1996, now Pat. No. 6,136,961.
(60) Provisional application No. 60/102,703, filed on Oct. 1, 1998, and provisional application No. 60/003,661, filed on Sep. 11, 1995.

(51) Int. Cl.$^7$ .................................................. C12P 7/62
(52) U.S. Cl. ...................... 435/135; 435/136; 435/117; 435/123; 435/72
(58) Field of Search .................................. 435/135, 136, 435/117, 123, 72

(56) References Cited

FOREIGN PATENT DOCUMENTS

WO9505475  2/1995  (WO).
WO 97/00233 * 3/1997  (WO).

OTHER PUBLICATIONS

J. Am. Chem. Soc. 119(47):11554–11555 (Khmelnitsky et al), 1997.*
Mathew et al, "Synthesis and Evaluation of Some Water–Soluble Prodrugs and Derivatives of Taxol with Antitumor Activity," *J. Med. Chem.*, 1992, 35, 145–151.
Deutsch et al., "Synthesis of Congeners and Prodrugs. 3. Water–Soluble Prodrugs of Taxol with Potent Antitumor Activity," *J. Med. Chem.*, 1989, 32, 788–792.
Ueda, et al. "Synthesis and Antitumor Evaluation of 2'–Oxycarbonylpaclitaxels (Paclitaxel–2'–Carbonates)," *Bioorg. Med. Chem. Lttrs.*, 1994, 4, 1861–1864.
Nicolaou et al., "Design, synthesis and biological activity of protaxols," *Nature*, Jul. 29, 1993, 364, 464–466.
Zhao et al., "Modified Taxols, 6. $^1$Preparation of Water–Soluble Prodrugs of Taxol," *J. Nat. Prod.*, Nov.–Dec. 1991, 54, 1607–1611.
Klibanov, "Asymmetric Transformations Catalyzed by Enzymes in Organic Solvents," *Acc. Chem. Res.*, 1990, 23, 114–120.

Hanson et al., "Site–specific Enzymatic Hydrolysis of Taxanes of C–10 and C–13," *J. Biol. Chem.*, Sep. 2, 1994, 269, 22145–22149.
Khmelnitsky et al., "Engineering biocatalytic systems in organic media with low water content," *Enzyme Microb. Technol.*, Dec. 1988,10, 710–724.
Lambusta, Daniela, et al., "Lipase catalyzed acylation of phenols in organic solvents," Indian Journal of Chemistry, vol. 32B, Jan. 1993, pp. 58–60.
Athawale, V.D. and Gaonkar, S.R., "Enzymatic Synthesis of Polyesters by Lipase Catalysed Polytransesterification," Biotechnology Letters, vol. 16, No. 2 (Feb. 1994), pp. 149–154.
Baldessari, Alicia et al., "Regioselective Acylation of 3–Mercaptopropane–1,2–diol by Lipase–catalysed Transesterification," J. Chem. Research (S), 1993, pp. 382–383.
Bianchi, Daniele et al., "Enzymatic preparation of optically active fungicide intermediates in aqueous and in organic media," Indian Journal of Chemistry, vol. 32B, Jan. 1993, pp. 176–180.
Bunnage, Mark E. et al., "Asymmetric Synthesis of the Taxol and Taxotère C–13 Side Chains," J. Chem. Soc. Perkin Trans. 1, 1994, pp. 238 239.
Chen, Ching–Shih and Sih, Charles J., "General Aspects and Optimization of Enantioselective Biocatalysis in Organic Solvents: The Use of Lipases," Angew. Chem. Int. Ed. Engl. 28 (1989), pp. 695–707.
Chmurney, Gwendolyn N. et al., "$^1$H– and $^{13}$C–NMR Assignments for Taxol, 7–epi–Taxol, and Cephalomannine," Journal of Natural Products, vol. 55, No. 4, Apr. 1992, pp. 414–423.
de Goede, A.T.J.W. et al., "Selective lipase–catalyzed 6–0–acylation of alkyl α–D–glucopyranosides using functionalized ethyl esters," Recueil des Travaux Chimiques des Pays–Bas, 112/11, Nov. 1993. pp 567–672.
Deutsch, H.M. et al., "Synthesis of Congeners and Prodrugs. 3. Water–Soluble Prodrugs of Taxol with Potent Antitumor Activity," Journal of Medicinal Chemistry, 1989, vol. 32, No. 4, pp. 792.
Dondoni, Alessandro et al., "Synthesis of Taxol and Taxotere Side chains by 2–(Trimethylsilyl)thiazole Based Homologation of L–Phenylglycine," Synthesis, Fab. 1995, pp. 181–186.
Fabre, Jean et al., "Regiospecific enzymic acylation of butyl α–D–glucopyranoside," Carbohydr. Res. 243 (1993) pp. 407–411.

(List continued on next page.)

Primary Examiner—Francisco Prats
(74) Attorney, Agent, or Firm—Nixon Peabody LLP

(57) ABSTRACT

A method for derivatizing a compound having a hydroxyl group by back to back acylation is provided. The compound is acylated with a bifunctional acyl donor in the presence of a hydrolase to form an activated acyl ester or carbonate. Preferably the bifunctional acylating donor is a di(vinyl) ester or carbonate. The activated acyl ester or carbonate is then used to acylate a nucleophile in the presence of a lipase. The method of the invention provides regioselective enzymatic acylation of the base compound.

8 Claims, No Drawings

OTHER PUBLICATIONS

Forastiere, Arlene A., "Use of Paclitaxel (TAXOL®) in Squamous Cell Carcinoma of the Head and Neck," Seminars in Oncology, vol. 20, No. 4, Suppl. 3 (Aug.), 1993, pp. 56–60.

Georg, Gunda I., "Synthesis of Biologically Active Taxol Analogues with Modified Phenylisoserine Side Chains," J. Med. Chem., 1982, vol. 35, No. 22.

Greenwald, Richard B. et al., "Highly Water Soluble Taxol Derivatives: 2'–Polyethyleneglycol Esters as Potential Prodrugs," Bioorganic & Medical Chemistry Letters, vol. 4, No. 20 (1994),pp. 2465–2470.

Guenard, Daniel et al., "Taxol and Taxotere: Discovery, Chemistry, and Structure—Activity Relationships," Acc. Chem. Res. 1993, 26, pp. 160–167.

Hanson, Ronald L. et al., "Site–specific Enzymatic Hydrolysis of Taxanes at C–10 and C–13," J. Biological Chemistry, vol. 269, No. 35, Issue of Sep. 2, pp. 22145–22148, 1994.

Herradon, Bernardo, "Biocatalytic Synthesis of Chiral Polyoxgenated Compounds: Effect of the Solvent on the Enantioselectivity of Lipase Catalyzed Transesterifications in Organic Solvents," SYNLETT, Feb. 1993, pp. 108–110.

Holton, Robert A., "First Total Synthesis of Taxol. 2. Completion of the C and D Rings," J. Am. Chem. Soc. 1994, 116, pp. 1599–1600.

Holton, Robert A., "First Total Synthesis of Taxol. 1. Functionalization of the B Ring," J. Am. Chem. Soc. 1994, 116, pp. 1597–1598.

Huang, C.H. Oliver et al., "New Taxanes from Taxus Brevifolia. 2.," J. Natural Products, vol. 49, No. 4, pp. 665–669, Jul.–Aug. 1986.

Ikeda, Isao and Klibanov, Alexander M., "Lipase–Catalyzed Acylation of Sugars Solubilized in Hydrophobic Solvents by Complexation," Biotechnology and bioengineering, vol. 42, pp. 788–791 (1993).

Jones, J. Bryan, "Enzymes in Organic Synthesis," Tetrahedron, vol. 42, No. 13, pp. 3351–3403, 1986.

Kanerva, Liisa T. and Sundholm, Oskari, "Enzymatic Acylation in the Resolution of Methyl threo–2–Hydroxy–3–(4–methoxyphenyl)–3–(2–X–phenylthio)propionates in Organic Solvents," J. chem. Soc. Perkins Trans. 1, 1993.

Kanerva, Liisa and Sundholm, Oskari, "Lipase Catalysis in the Resolution of Recemic Intermediates of Diltiazem Synthesis in Organic Solvents," J. Chem. Soc. Perkin Trans. 1., 1993.

Khmelnitsky, Yuri L., "Salts Dramatically Enhance Activity of Enzymes Suspended in Organic Solvents," J. Am. Chem. Soc., 1994, 116.

Khmelnitsky, Yu. L., "Engineering biocatalytic systems in organic media with low water contents," Enzyme Microb. Technol., 1988, vol. 10, Dec., pp. 710–724.

Kingston, David G.I. et al., "The Chemistry of Taxol, a Clinically Useful Anticancer Agent," J. Natural Products, vol. 53, No. 1, pp. 1–12, Jan.–Feb. 1990.

Kingston, David G.I. et al., "Synthesis of Taxol from Baccatin III via an Oxazoline Intermediate," Tetrahedron Letters, vol. 35, No. 26, pp. 4483–4484, 1994.

Kingston, David G.I., "The Chemistry of Taxol," Pharmac. Ther., vol. 52, pp. 1034, 1991.

Kingston, David G.I., "Taxol: the chemistry and structure—activity relationships of a novel anticancer agent," Tib. Tech. 12(6), 1994, pp 222–227.

Yong–Fu Li and Hammerschmidt, Friederich, "α–(Acyloxy-)phosphonates by Esterolytic Enzymes," Tetrahedron:Asymmetry, vol. 4, No. 1, pp. 109–120, 1993.

Ljunger, Gudrun et al., "Lipase Catalyzed Acylation of Glucose," Biotechnology Letters, vol. 16, No. 11 (Nov. 1994), p. 1167–1172.

Lopez, Rosa et al., "Enzymatic Transesterification of Alkyl 2,3,4–Tri–O–Acyl–β–D–Xylopyranosides," J. Carbohydrate Chemistry, 12(2), 165–171 (193).

Magri, Neal F. and Kingston, David G.I., "Modified Taxols, 4.Synthesis and Biological Activity of Taxols Modified in the Side Chain," J. Natural Products, vol. 51, No. 2, pp. 298–306, Mar.–Apr. 1988.

Mamber, Stephen W. et al., "Tubulin Polymerization by Paclitaxel (Taxol) Phosphate Prodrugs after Metabolic Activation with Alkaline Phosphatase," J. Pharmacology and Experimental Therapeutics, vol. 274, No. 2, 1995, pp. 877–883.

Mathew, Abraham E., "Synthesis and Evaluation of Some Water–Soluble Prodrugs and Derivatives of Taxol with Antitumor Activity," J. Med. Chem. 1992, 35, 145–151.

Matzner, Markus et al., "The Chemistry of Chloroformates," Chemical Reviews, vol. 64, No. 6, Dec. 1964, 645–687.

McGuire, William P. et al., "Taxol: A Unique Antineoplastic Agent with Significant Activity in Advanced Ovarian Epithelial Neoplasms," Annals of Internal Medicine, vol. 111, No. 4, 273–280.

Mellado, Wilfredo et al., "Preparation and Biological Activity of Taxol Acetates," Biochemical and biophysical Research Communications, vol. 124, No. 2, 1984, pp. 329–336.

Menendez, Emma and Gotor, Vicente, Acylation and Alkoxycarbonylation of Oximes Through an Enzymatic Oximolysis Reaction, Synthesis, Jul. 1993, 72–74.

Nicolaou, Kyriacos Costa et al., "Synthesis of C–2 Taxol Analogues," Angew. Chem. Int. Ed. Engl. 1994, 33, No. 15.16, pp. 1581–1582.

Nicolaou, K.C. et al., "Total Synthesis of Taxol. 1. Retrosynthesis, Degradation, and Reconstitution," J. Am. Chem. Soc. 1995, 117, 624–633.

Nicolaou, K.C. et al., "Design, synthesis and biological activity of protaxols," Nature, vol. 364, Jul. 29, 1993, 464–466.

Ojima, Iwao et al., "New and Efficient Approaches to the Semisynthesis of Taxol and its C–13 Side Chain Analogs by Means of β–Lactam Synthon Method," Tetrahedron, vol. 48, No. 34, pp. 6985–7012, 1992.

Panza, Luigi et al., "Selective Acylation of 4,6–O–Benzylidene Glycopyranosides by Enzymatic catalysis," J. Carbohydrate Chemistry, 12(1), 125–130 (1993).

Ringel, Israel and Horwitz, Susan Band, "Taxol is Converted to 7–Epitaxol, a Biologically Active Isomer, in Cell Culture Medium," The Journal Pharmacology and Experimental Therapeutics, vol. 242, 1987, pp. 692–698.

Rowinsky, Eric K. et al., "Taxol: A Novel Investigational Antimicrotubule Agent," J. Nat. Cancer Inst., vol. 82, No. 15, Aug. 1, 1990, pp. 1247–1250.

Rowinsky, Eric K. et al., "Taxol: The First of the Taxanes, an Important New Class of Antitumor Agents," Seminars In Oncology, vol. 19, No. 6 (Dec.), 1992, pp. 646–662.

Schiff, Peter B. et al., "Promotion of microtubule assembly in vitro by taxol," Nature, vol. 277, Feb. 22, 1979, p. 665–667.

Schlotterbeck, Andrea et al., "Lipase–Catalyzed Monoacylation of Fructose," Biotechnology Letters, vol. 15, No. 1 (Jan. 1993) pp. 61–64.

Sharma, A. and Chattopadhyay, S., "Lipase Catalysed Acetylation of Carbohydrates," Biotechnology Letters, vol. 15, No. 11 (Nov. 1993), pp. 1145–1146.

Sih, Charles J. and Rosazza, John P., "Microbial Transformations in Organic Synthesis," Techniques of Chemistry, vol. X—Applications of Biochemical Systems in Organic Chemistry, 1976, pp. 69–106.

Therisod, Michel and Klibanov, Alexander M., "Facile Enzymatic Preparation of Monoacylated Sugars in Pyridine," J. Am. Chem. Soc., vol. 108, No. 18, 1986, pp 5638–5640.

Ueda, Yasutsugu et al., Synthesis and Antitumor Evaluation of 2'–Oxycarbonylpaclitaxels (Paclitaxel–2'–Carbonates), Biorganic & Medicinal Chemistry Letters, vol. 4, No. 15, pp. 1861–1864. (1994).

Ueda, Yasutsugu et al., "Novel, Water–soluble Phosphate Derivatives of 2'–Ethoxy Carbonylpaclitaxel as Potential Prodrugs of Paclitaxel: Synthesis and Antitumor Evaluation," Biorganic & Medicinal Chemistry Letters, vol. 5, No. 3, pp. 247–252, 1995.

* cited by examiner

TWO STEP ENZYMATIC ACYLATION

CROSS-REFERENCE TO RELATED APPLICATION(S)

This application claims priority from U.S. Provisional Patent Application No. 60/102,703. filed Oct. 1, 1998, and is a continuation-in-part of U.S. patent application Ser. No. 09/091,833, filed Jun. 29, 1998, now U.S. Pat. No. 6,136, 961, issued Oct. 24, 2000, which claims priority to PCT/US 96/14573, filed Sep. 11, 1996, which claims priority to U.S. Provisional Patent Application No. 60/003,661, filed Sep. 11, 1995.

BACKGROUND OF THE INVENTION

There are many pharmaceuticals which are not substantially soluble in water and this lace of solubility limits the usefulness of these pharmaceuticals. For example, in many cases a pharmaceutical which might otherwise be administered intramuscularly or intraperitoneally might be administered orally or intravenously if the pharmaceutical were water soluble.

SUMMARY

The present invention provides a method for modifying the solubility of pharmaceuticals through back to back acylation reactions using a bifunctional acylating agent. It has been found that compounds such as paclitaxel, bergenin, erythromycin and adenosine which contain a neuclephilic group in the molecule that is amenable to enzymatic acylation will react regiospecifically with a bifunctional acylating agent in the presence of a hydrolytic enzyme such as a lipase or protease enzyme. Preferably the bifunctional acylating agent is a di(vinyl) ester or carbonate. This yields a vinyl ester or vinyl carbonate derivative which can be subsequently hydrolyzed or reacted with nucleophiles such as alcohols, sugars and amines.

In accordance with a preferred embodiment of the invention, the method is used to produce derivatives of paclitaxel and, more particularly, water soluble derivatives of paclitaxel. The present invention also provides derivatives of paclitaxel, bergenin, erythromycin and adenosine.

DETAILED DESCRIPTION

Representative examples of bifunctional acylating agents include di(vinyl) or di(2,2,2-trifluoroethyl) esters of dicarboxylic acids or di(vinyl) carbonates of dialcohols.

The bifunctional acylating agents useful in the present invention include compounds of the formulas (I), (II) and (III) and their equivalents:

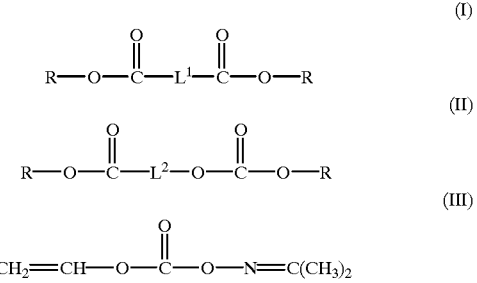

wherein $L^1$ and $L^2$ are linking groups, R is vinyl or trifluoroethyl. Those skilled in the art will recognize that a wide range of linking groups may be useful and that other R groups which activate the acyl group will also be useful.

Typically, $L^1$ is a linking group such as a straight chain or a branched chain or a cyclic alkylene having 1 to 10 and preferably 1 to 8 carbon atones or a direct bond and $L^2$ is a linking group such as a straight chain, branched chain or cyclic alkylene having 2 to 10 and preferably 2 to 8 carbon atoms or a linkage including a saturated or unsaturated heterocyclic ring such as tetrahydrofuranyl or pyridinyl. Specific examples of $L^1$ include trimethylene, tetramethylene, hexamethylene, cyclohexylene, phenylene, and propylenylene. Specific examples of $L^2$ include trimethylene, tetramethylene hexamethylene, 2-butenylene, propylenylene, 1,3-dimethylene cyclohexylene, 1,4-dimethylene cyclohexylene, 2, 5-dimethylenefuranyl and 2,6-dimethylene pyridinyl.

Specific bifunctional acylating agents useful in the invention include: adipic acid divinyl ester; 1,3-propanediol di(vinyl carbonate); 1,4-butanediol di(vinyl carbonate); acetone oxime vinyl carbonate; 1,4-cyclohexane dimethanol di(vinyl carbonate); 1,6-hexanediol di(vinyl carbonate); 2,5-furandimethanol di(vinyl carbonate); 2,6-pyridine dimethanol di(vinyl carbonate); 1,4-but-2-enediol di(vinyl carbonate); oxalic acid di(trifluoroethyl) ester; 1,4-cyclohexane dicarboxylic acid di(trifluoroethyl) ester; terephthalic acid di(trifluoroethyl) ester and 1,3-propylenediol di(vinyl carbonate).

The back to back acylation reactions are conducted in the presence of a hydrolase, such as a lipase or a protease enzyme. Preferably the enzymes have been lyophilized in the presence of simple salts to enhance catalytic activity in organic solvents. U.S. Pat. No. 5,449,613 to Dordick et al. (incorporated herein by reference) discloses a method for reacting an enzyme in a non-aqueous media comprising the steps of first preparing a lyophilizate of an enzyme and a salt wherein the lyophilizate contains a salt in a weight ratio sufficient to activate the enzyme in an organic solvent and then dispersing the lyophilizate in a non-aqueous, organic solvent in the presence of a substrate for the enzyme. More preferably, the enzyme is activated by dissolving the enzyme and a salt capable of activating the enzyme in an aqueous solution and then lyophilizing for a period of time sufficient to maximize the activity of the enzyme.

Representative examples of hydrolases useful in the present invention include proteases such as thermolysin from *Bacillus thermoproteolyticus rokko* and subtlisin Carlsberg from *Bacillus lichiniformis*. Additionally, pH adjusted proteases/esterases (Type XIII from *Aspergillus saitol*, Newlase, ficin, Solvay fungal protease 31000, alkaline protease, papain 16,000, Prozyme 6, Prozyme N, Prozyme S, Biozyme M2 and bromelain) may also be used.

Representative examples of lipases include those from *Candida antarctica, Pseudomonas cepacia, Rhizopus oryzae, Mucor meihei*, Pseudomonos sp., *Humicola lanuginosa* (type CE), Alcaligences sp., *Geotrichium candidum* (type GC4), Rhizopus sp., *Rhizopus arrhizus, Rhizopus javanicus, Rhizopus delemar, Candida lipolytica* (type L-10), *Aspergillus niger* (type AP-12), porcine pancreas, and *Chromobacterium viscosum*.

The reaction product of the bifunctional acylating agent can be hydrolyzed by reaction with water or it can be reacted with a nucleoplile. The activated ester or carbonate produced in the first acylation is reactive with a variety of nucleophiles. Representative examples of nucleophiles that can be acylated with the activated ester or carbonate of the present invention include water, sugars, alcohols, amines and aminoalcohols.

Representative examples of sugars include: glucose, galactose, mannose, fructose, 1,2:3,4-di-O-isopropylidene-D-galactopyranose, deoxynojirimycin, D-fucose, and N-acetyl-D-glucosamine.

Representative examples of alcohols include: (±)-1,3, butanediol, (±)-2-butanol, (±)-menthol, 1-(2-hydroxyethyl)-

2-pyrrolidinone, 1,4-butanediol, 1-aziridineethanol, 1-butanol, 1-methyl-3-piperidinemethanol, 1-octanol, 2-(methylsulfonyl)ethanol, 2-naphthaleneethanol, 3,3-diethoxy-1-propanol, 3-thiophenemethanol, 4-chlorobenzyl alcohol, 4-hydroxybenzyl alcohol, 4-methoxybenzyl alcohol, 4-methyl-5-thiazoleethanol, 5-methyltetrahydrofuran-2-methanol, benzyl alcohol, furfuryl alcohol, glycidol, phenethyl alcohol and sec-phenethyl alcohol.

Representative examples of amines include: (aminomethyl)cyclopropane, 1-(2-aminoethyl)piperazine, 1-(2-aminoethyl)pyrrolidine, 1-(3-aminopropyl)imidazole, 1-butylamine, 1-(aminomethyl)naphthalene, 2-(2-aminoethyl)-1-methylpyrrolidine, 2-aminomethyl benzodioxane, 2-(aminomethyl)thiophene, 3-(aminomethyl) pyridine, 3,3-dimethylbutylamine, 3-dimethylamninopropylamine, 4-chlorobenzyl amine, 4-phenylbutylamine, benzylamine, cyclohexylamine, furfurylamine, hexylamine, and tetrahydrofurfurylamine.

Representative examples of aminoalcohols include: 2-amino-2-methyl-1-propanol, 3-amino-1-propanol, ethanolamine, 4-amino-2-butanol, and (±)-2-amino-1-butanol.

The reactions of the invention are typically carried out in a solvent. Representative examples of solvent useful in the present invention include tert-amyl alcohol, butyl acetate, acetonitrile, toluene, hexane, tert-butyl methyl ether, 2-pentanone, tetrahydrofuran, 1,4-dioxane, dimethylsulfoxide (DMSO) and mixtures thereof.

The method of the invention is typically conducted in accordance with the following procedure. The base compound and bifunctional acylating agent are admixed in solvent to form a solution. This solution is added to solid enzyme and reacted at 37° C. to 60° C. with 250 rpm shaking for 1 to 7 days to yield an activated acyl ester or carbonate. The activated acyl ester or carbonate is purified by preparative reversed phase HPLC and then dissolved in an appropriate solvent, typically acetonitrile or tert-butyl alcohol. The resulting solution is added to dry enzyme and nucleophile and allowed to react at 37° C. to 60° with 250 rpm shaking for 1 to 15 days to produce the derivatives of the present invention.

EXAMPLE 1

Paclitaxel is a powerful antimitotic agent that acts by promoting tubulin assembly into stable aggregated structures. Although paclitaxel has shown tremendous potential as an anticancer compound, its use as a cancer drug is compromised by its poor aqueous solubility. Paclitaxel can be enzymatically derivatized in an organic solvent in accordance with the present invention to generate derivatives possessing high solubility in water. This embodiment of the invention involves back to back acylation as depicted in the following scheme. In the first step paclitaxel is reacted in the presence of an enzyme with a bifunctional acylating agent to give an activated acyl derivative, which is then used as a complex acyl donor in the second step of the derivatization procedure.

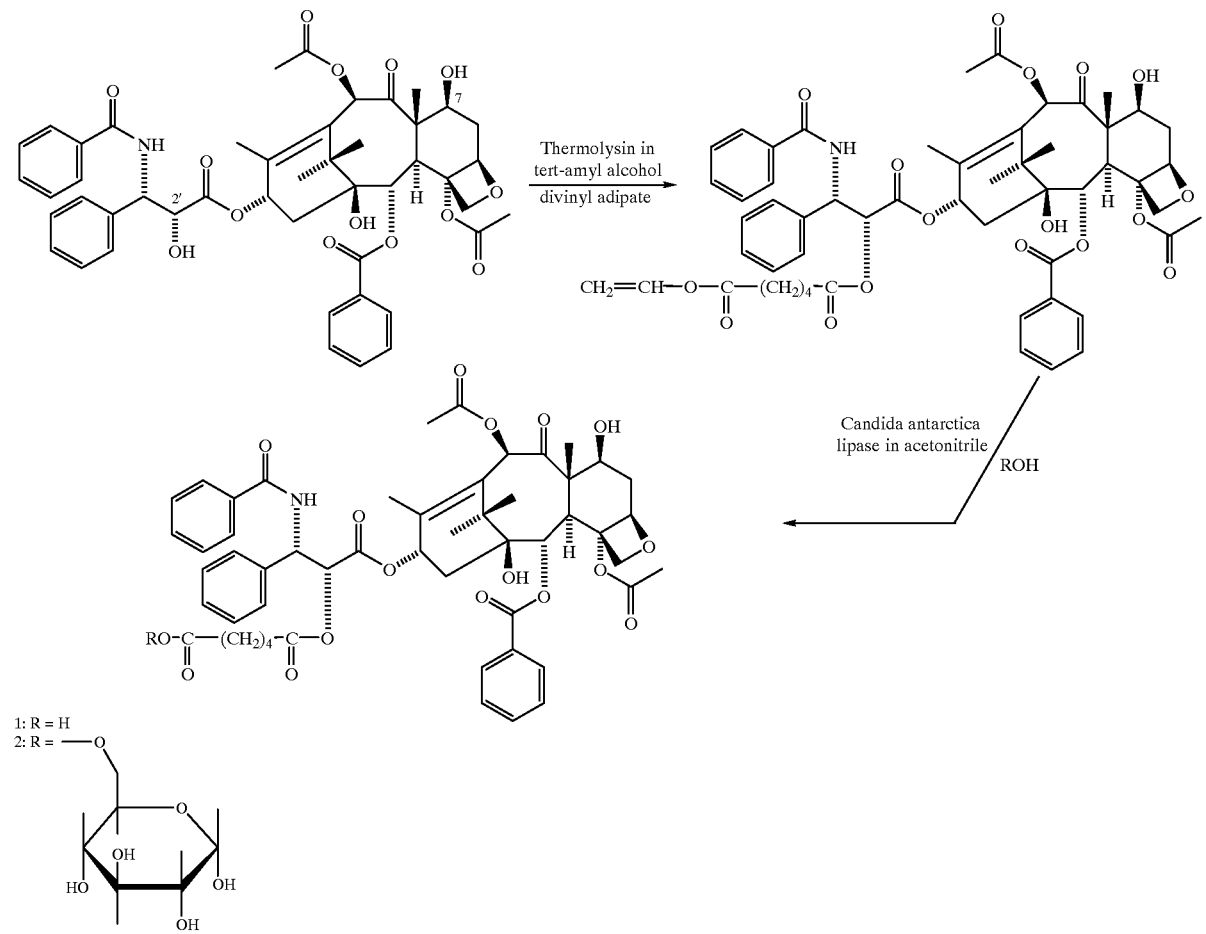

Enzymes found to possess paclitaxel acylation activity included α-chymotrypsin, subtilisin Carlsberg and thermolysin. Among these enzymes thermolysin showed the highest activity (ca. 3-and 40-fold higher than α-chymotrypsin and subtilisin, respectively). The reactivity of thermolysin toward paclitaxel was enhanced ca. 20-fold by lyophilizing the enzyme in the presence of KCl prior to use.

The bifunctional acylating agents useful in acylating paclitaxel include acetone oxime vinyl carbonate (III) and compounds of the formulas (IA) and (II A) and their equivalents:

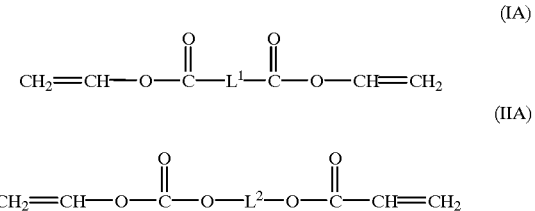

Representative bifunctional acylating agents particularly useful in acylating paclitaxel include: adipic acid divinyl ester; 1,3-propanediol di(vinyl carbonate); 1,4-butanediol di(vinyl carbonate); acetone oxime vinyl carbonate, 1,4-cyclohexane dimethanol di(vinyl carbonate), 1,6-hexanediol di(vinyl carbonate), 2,5-furandimethanol di(vinyl carbonate), 2,6-pyridine dimethanol di(vinyl carbonate), and 1,4-but-2-enediol di(vinyl carbonate).

Representative solvents useful in the acylation of paclitaxel include: tert-amyl alcohol, butyl acetate, acetonitrile, toluene, hexane, tert-butyl methyl ether, 2-pentanone, tetrahydrofuran, 1,4-dioxane and mixtures thereof.

The enzyme catalyzed acylation of paclitaxel with a bifunctional acylating agent can be carried out by adding a solution of paclitaxel (1 to 15 mM) and bifunctional acylating agent (2 to 50 equivalents) in solvent to the salt activated enzyme (10–80 mg/ml). The resultant solution was reacted at 37° C. to 60° C. with 250 rpm shaking for 1 to 7 days to produce an activated paclitaxel ester or carbonate acylated at the 2' position. Thermolysin is an extremely regioselective enzyme toward the 2' hydroxyl moiety of paclitaxel as no other hydroxyl groups on the paclitaxel molecule were esterified in the enzymatic reaction.

The activated paclitaxel ester or carbonate functions as an acyl donor in the second step of the back to back acylation. The activated paclitaxel 2' derivative was purified by preparative HPLC and used as the acyl donor for transesterification in dry solvent containing a nucleoplile as the acyl acceptor and lipase from *Candida antarctica* as the catalyst. Nucleophiles typically used include sugars (glucose, mannose and fructose) and alcohols (1-butanol). Acetonitrile dried over molecular sieves is the preferred solvent.

A solution of the purified activated paclitaxel ester or carbonate (5 to 20 mM) in dry solvent was added to solid enzyme (50–75 mg/ml) and nucleophile (8 to 10 equivalents). The resultant solution was reacted at 37° C. to 60° C. with 250 rpm shaking for 1 to 7 days to produce the paclitaxel derivatives of the invention.

Acylation of paclitaxel with adipic acid divinyl ester results in the formation of predominantly paclitaxel 2'-vinyl adipate (60% yield) and a minor amount of 7-epipaclitaxel 2'-vinyl adipate (18% yield). (Epimerization of paclitaxel to 7-epi-paclitaxel occurs spontaneously under reaction conditions.) Acylation of glucose with the purified paclitaxel 2'-vinyl adipate results in the formation of paclitaxel 2'-adipoylglucose with 85% isolated yield (presumably linked selectively to the 6-hydroxyl moiety of the sugar). Paclitaxel 2'-adipoylmannose and paclitaxel 2'-adipoylfructose were also synthesized using a similar procedure starting with paclitaxel 2'-vinyl adipate and the corresponding sugar.

Alternatively, the activated paclitaxel ester or carbonate can be hydrolyzed to form an acid. For example, a solution of paclitaxel ester (5 to 20 mM 2'-vinyl adipate) in solvent and water (1% v/v) was added to solid enzyme (50–75 mg/ml). The resultant solution was reacted at 37° C. to 60° C. with 250 rpm shaking for 1 to 7 days to give paclitaxel 2'-adipic acid with 75% isolated yield.

This two step process of the invention demonstrates the unique advantage of enzymatic catalysis, namely the high regioselectivity of hydrolysis/transesterification to generate paclitaxel derivatives. Both the free adipic acid and sugar-containing paclitaxel derivatives were more soluble in water than paclitaxel itself. Specifically, the solubility of paclitaxel (<4 μg/ml) is increased 58-fold and 1625-fold for the paclitaxel 2'(adipoyl) glucose and paclitaxel 2'-adipic acid, respectively. Thus, the enzymatic addition of polar functionalitites onto the 2'-position of paclitaxel results in dramatic improvement of paclitaxel's water solubility.

EXAMPLE 2

Bergenin is a naturally occuring polyhydroxylated flavonoid. The chemical structure for bergenin is:

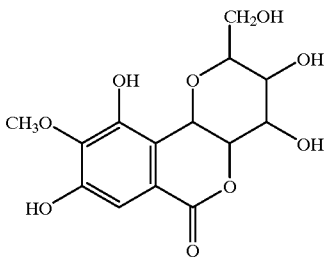

Enzymes found to possess bergenin acylation activity included lipases from *Pseudomonas cepacia* and *Rhizopus oryzae* (both immobilized by adsorption on the polypropylene support, Accurel), lipases from *Candida antarctica* and *Mucor meihei* (immobilized on a polymeric support by producer), porcine liver esterase (straight from the bottle or pH adjusted with 95% KCl), and subtilisin Carlsberg (protease from *Bacillus licheniformis*; straight from the bottle or pH adjusted with 95% KCl).

Representative solvents useful during the acylation of bergenin include toluene/5% DMSO (v/v), tetrahydrofuran, acetonitrile and mixtures thereof.

Representative bifunctional acylating agents useful in the acylation of bergenin include: adipic acid divinyl ester; oxalic acid di(trifluoroethyl) ester, 1,4-cyclohexane dicarboxylic acid di(trifluoroethyl)ester, 2,5-furan dimethanol di(vinyl carbonate), terephthalic acid di(trifluorethyl)ester, acetone oxime vinyl carbonate, 1,3-propylenediol di (vinyl carbonate), 1,4-cyclohexane dimethanol di(vinyl carbonate) 1,6-hexanediol di(vinyl carbonate), 2,6-pyridine dimethanol di(vinyl carbonate), and 1,4-but-2-enediol di(vinyl carbonates.

Bergenin was acylated by adding a solution of bergenin (10 to 20 mM) and bifunctional acylating agent (1.1 to 25 equivalents) in solvent dried over molecular sieves to solid enzyme (30 mg/ml). The resultant solution was reacted at 45° C. with 250 rpm shaking for 1 to 7 days to produce an activated bergenin ester or carbonate.

The activated bergenin ester or carbonate was used as an acyl donor for transesterification in dry solvent containing a nucleophile as the acyl acceptor. Enzymes typically used to catalyze the reaction include lipases from *Pseudomonas cepacia* and Pseudomonas sp. (both immobilized by adsorption on polypropylene support, Accurel) and lipases from *Candida antarctica* and *Mucor meihei* (immobilized on a polymeric support by producer).

Representative nucleophiles include sugars, amines, alcohols and aminoalcohols. Representative sugars include: glucose, galactose, mannose, fructose, 1,2:3,4-di-O-isopropylidene-D-galactopyranose.

Representative amines include: (±)-2-amino-1-butanol, (aminomethyl)cyclopropane, 1-(2-aminoethyl)piperazine, 1-(2-aminoethyl)pyrrolidine, 1-(3-aminopropyl)imidazole, 1-butylamine, 1-(aminomethyl)naphthalene, 2-(2-aminoethyl)-1-methylpyrrolidine, 2-aminomethyl benzodioxane, 2-(aminomethyl)thiophene, 3-(aminomethyl) pyridine, 3,3-dimethylbutylamine, 3-dimethylaminopropylamine, 4-chlorobenzyl amine, 4-phenylbutylamine, benzylamine, cyclohexylamine, furfurylamine, hexylamine, and tetrahydrofurfurylamine.

Representative alcohols include: (±)-1,3-butanediol, (±)-2-butanol, (±)-menthol, 1-(2-hydroxyethyl)-2-pyrrolidinone, 1,4-butanediol, 1-aziridineethanol, 1-butanol, 1-methyl-3-piperidinemethanol, 1-octanol, 2-(methylsulfonyl)ethanol, 2-naphthaleneethanol, 3,3-diethoxy-1-propanol, 3-thiophenemethanol, 4-chlorobenzyl alcohol, 4-hydroxybenzyl alcohol, 4-methoxybenzyl alcohol, 4-methyl-5-thiazoleethanol, 5-methyltetrahydrofuran-2-methanol, benzyl alcohol, furfuryl alcohol, glycidol, phenethyl alcohol, and sec-phenethyl alcohol.

Representative amino alcohols include: 2-amino-2-methyl-1-propanol, 3-amino-1-propanol, ethanolamine, and 4-amino-2-butanol.

A solution of the purified activated bergenin ester or carbonate (5 mM) in dry solvent (preferably acetonitrile dried over molecular sieves) was added to a solid enzyme (10–50 mg/ml) and nucleophile (two equivalents). The resultant solution was reacted at 45° C. with 250 rpm shaking for 3 to 15 days to produce the bergenin derivatives of the invention. Alternatively, the activated bergenin ester or carbonate can be hydrolyzed to form an acid. For example, a solution of bergenin ester or carbonate (5 mM) in solvent and 1% (v/v) water was added to solid enzyme (10 to 50 mg/ml). The resultant solution was reacted at 45° C. with 250 rpm shaking for 1–7 days to give the bergenin acid derivative.

EXAMPLE 3

Erythromycin is a bacteriostatic macrolide antibiotic isolated from a soil bacterium (*Streptomyces erythreus*), used in treatment of various bacterial diseases. The base, the stearate salt, and the esters are poorly soluble in water. The chemical stricture for erythromycin is:

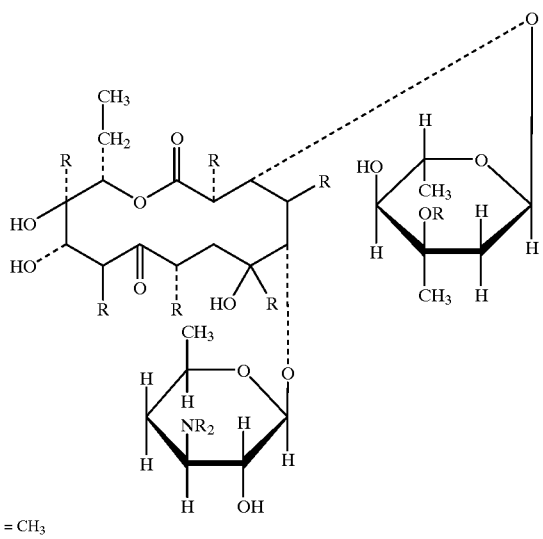

R = CH₃

Erythromycin was acylated by adding a solution of erythromycin (50 mM) and adipic acid divinyl ester (1 M) in acetonitrile/10% DMSO (v/v) dried over molecular sieves to solid enzyme (40 mg each enzyme/20 ml reaction). The resultant solution was reacted at 45° C. with 250 rpm shaking for 1 to 7 days to produce an activated erythromycin ester.

Enzymes found to posses erthromycin acylation activity included: lipases from *Humicola lanuginosa* (type CE), porcine pancreas (type 250 and type II), Pseudomonas sp. (Type CES), Alcaligenes sp., *Geotrichium candidum* (type GC4), Rhizopus sp., *Rhizopus arrhizus, Rhizopus javanicus, Rhizopus delemar, Candida lipolytica* (type L-10), *Aspergillus niger* (type AP-12); pH adjusted proteases/esterases (Type XIII from *Aspergillus saitol*, Newlase, ficin, Solvay fungal protease 31000, alkaline protease, papain 16000, Prozyme 6, Prozyme N, Biozyme S, Biozyme M2, and bromelain).

The activated erythromycin ester was purified and used as the acyl donor for the acylation of sugars. Erythromycin ester (5 mM) and sugar (100 mM) were added to solid enzyme (50 mg). 4.96 μl of triethylamine were also added for the acylation of deoxynojirimycin. The resultant solution was reacted as 45° C. with 250 rpm shaking for 1 to 7 days to produce the erythromycin derivative.

Enzymes useful for the acylation of sugars with erythromycin ester include lipase from *Candida antarctica* (immobilized on a polymeric support by producer) and lipase from Pseudomonas sp. (Type AK). Preferred solvents include: acetonitrile and tert-butyl alcohol dried over molecular sieves.

EXAMPLE 4

Adenosine is a ribonucleoside which consists of the nitrogenous base adenine linked to the sugar ribose. The chemical structure for adenosine is:

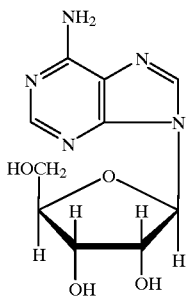

Enzymes found to possess adenosine acylation activity included: lipases from *Chromobacterium viscosum* and *Geotrichum candidum* (both immobilized by adsorption on polypropylene support, Accurel), subtilisin Carlsberg (protease from *Bacillus licheniformis*, straight from the bottle or pH adjusted with 95% KCl), and thermolysin (protease from *B. thermoproteolyticus rokko*, straight from the bottle or pH adjusted with 95% KCl).

Representative bifunctional acylating agents useful in the acylation of adenosine include: 1,4-but-2-enediol di(vinyl carbonate), 1,4-cyclohexane dicarboxylic acid ditrifluoroethyl ester, 1,6-hexanediol di(vinyl carbonate), 2,5-furandimethanol di(vinyl carbonate), 2,6-pyridine dimethanol di(vinyl carbonate), acetone oxime vinyl carbonate, adipic acid divinyl ester, and terephtalic acid ditrifluoroethyl ester.

Adenosine was acylated by adding a solution of adenosine (20 mM) and bifunctional acylating agent (5 equivalents) in acetonitrile dried over molecular sieves to solid enzyme (100 mg/ml). The resultant solution was reacted at 45° C. with 250 rpm shaking for 1 to 7 days to produce an activated adenosine ester or carbonate.

The activated adenosine ester or carbonate was purified and used as the acyl donor for transesterification in dry acetonitrile with added molecular sieves containing a nucleophile as the acyl acceptor. Enzymes useful in catalyzing the reaction include: lipases from *Pseudomonas cepacia*, Pseudomonas sp., porcine pancreas, and *Rhizopus arrhizus* (immobilized by adsorption on polypropylene support, Accurel), and lipases from *Candida antarctica* and *Mucor meihei* (immobilized on a polymeric support by producer).

Nucleophiles typically used as acyl acceptors include amines, alcohols and aminoalcohols. Representative amines include: 1-(2-aminoethyl)piperazine, 1-(3-aminopropyl) imidazole, 1-butylamine, 2-(2-aminoethyl)-1-methylpyrrolidine, 2-aminomethyl benzodioxane, 2-(aminomethyl)thiophene, 3,3-dimethylbutylamine, 3-dimethylaminopropylamine, 4-chlorobenzyl amine, 4-phenylbutylamine, cyclohexylamine, furfurylamine, and tetrahydrofurfurylamine, and hexylamine.

Representative alcohols include: (±)-1,3-butanediol, (±)-menthol, 1-(2-hydroxyethyl)-2-pyrrolidinone, 1,2:3,4-di-O-isopropylidene-D-galatopyranoside, 1-methyl-3-piperidinemethanol, 2-(methylsulfonyl) ethanol, naphthaleneethanol, 3-thiophenemethanol, 4-amino-2-butanol, 4-methoxybenzyl alcohol, 5-methyltetrahydrofuran-2-methanol, furfuryl alcohol, glycidol, phenethyl alcohol, and sec-phenethyl. Representative amino alcohols include: (±)-2-amino-1-butanol.

A solution of the purified activated adenosine ester or carbonate (5 mM) in dry acetonitrile with added molecular sieves was added to solid enzyme (10–50 mg/ml) and nucleophile (4 equivalents). The resultant solution was reacted at 45° C. with 250 rpm shaking, for 3–15 days to produce the adenosine derivatives of the invention.

While the invention has been illustrated using paclitaxel, bergenin, erythromycin, and adenosine, those skilled in the art will recognize that derivatives of these compounds can also be reacted in accordance with this invention. Those skilled in the art will recognize that the two step enzymatic acylation of the present invention is applicable to any molecule that can be enzymatically acylated regardless of its specific structure provided that the molecule bears a nucleophilic group, such as hydroxyl, amine, or thiol amenable to enzymatic acylation. Having described the invention in detail, it will be apparent that modifications and variations are possible without departing from the scope of the invention as defined by the following claims.

What is claimed is:

1. A method which comprises acylating paclitaxel with a bifunctional acyl donor in the presence of a hydrolytic enzyme to form an activated acyl ester or carbonate of paclitaxel and acylating a nucleophile with said activated acyl ester or carbonate in the presence of a hydrolytic enzyme.

2. The method of claim 1 wherein said bifunctional acyl donor is a divinyl ester of a dibasic acid.

3. The method of claim 1 wherein said bifunctional acyl donor is acetone oxime vinyl carbonate or a compound of the formula I(A) or II(A)

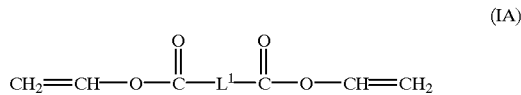

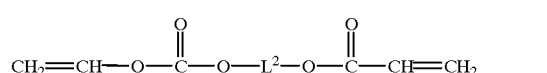

where L is a linking group.

4. The method of claim 3 wherein said bifunctional acyl donor is selected from the group consisting of adipic acid divinyl ester; 1,3-propanediol di(vinyl carbonate); 1,4-butanediol di(vinyl carbonate); 1,4-cyclohexane dimethanol di(vinyl carbonate), 1,6-hexanediol di(vinyl carbonate), 2,5-furandimethanol di(vinyl carbonate), 2,6-pyridine dimethanol di(vinyl carbonate), and 1,4-but-2-enediol di(vinyl carbonate).

5. The method of claim 1 wherein said nucleophile is a sugar or butanol.

6. The method of claim 5 wherein said sugar is selected from the group consisting of glucose galactose, mannose, fructose, 1,2:3,4-di-O-isopropylidene-D-galactopyranose.

7. The method of claim 1 wherein said nucleophile is acylated with said activated acyl ester or carbonate in the presence of a lipase from *Candida antarctica*.

8. The method of claim 1 wherein said paclitaxel is acylated with a bifunctional acyl donor in the presence of a thermolysin from *Bacillus thermoprotelyticus rokko*.

* * * * *